(12) United States Patent
Vogt

(10) Patent No.: US 9,220,853 B2
(45) Date of Patent: Dec. 29, 2015

(54) LAVAGE SYSTEM HAVING A NOZZLE

(71) Applicant: Heraeus Medical GmbH, Wehrheim (DE)

(72) Inventor: Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 320 days.

(21) Appl. No.: 13/873,675

(22) Filed: Apr. 30, 2013

(65) Prior Publication Data
US 2013/0331772 A1 Dec. 12, 2013

(30) Foreign Application Priority Data

May 7, 2012 (DE) .......................... 10 2012 013 464

(51) Int. Cl.
*A61M 11/00* (2006.01)
*A61M 11/02* (2006.01)
*B05B 7/24* (2006.01)
*B05B 15/02* (2006.01)
*B05B 15/04* (2006.01)
*A61M 1/00* (2006.01)
(Continued)

(52) U.S. Cl.
CPC ............. *A61M 11/02* (2013.01); *A61M 1/0064* (2013.01); *A61M 3/0233* (2013.01); *A61M 3/0283* (2013.01); *B05B 7/2421* (2013.01); *B05B 7/2435* (2013.01); *B05B 15/02* (2013.01); *B05B 15/0425* (2013.01); *A61B 2017/0023* (2013.01); *B05B 7/12* (2013.01); *B05B 12/002* (2013.01)

(58) Field of Classification Search
CPC . A61M 1/0064; A61M 1/0084; A61M 11/06; A61M 11/002
See application file for complete search history.

(56) References Cited

U.S. PATENT DOCUMENTS 4,228,795 A 10/1980 Babington
4,278,078 A 7/1981 Smith
(Continued)

FOREIGN PATENT DOCUMENTS

CN 1238007 A 12/1999
DE 2039370 A1 2/1972
(Continued)

OTHER PUBLICATIONS

Sherman, et al., "The Role of Lavage in Preventing Hemodynamic and Blood-Gas Changes During Cemented Arthroplasty," The Journal of Bone and Joint Surgery, Incorporated; Apr. 1983, vol. 65-A, No. 4, pp. 500-506, Toronto, Ontario, Canada.
(Continued)

*Primary Examiner* — Aarti B Berdichevsky
(74) *Attorney, Agent, or Firm* — Norris McLaughlin & Marcus, P.A.

(57) ABSTRACT

A medical spray device has a compressed gas supply conduit for guiding a gas flow, a liquid supply conduit for supplying a liquid, a dispensing tube having an open tube end for spraying fine droplets or a spray mist of a liquid-gas mixture, and an operable valve element that is arranged in the compressed gas supply conduit. A constriction of the cross-sectional area is provided in the dispensing tube and a merging site is arranged in the region of the constriction through which the liquid merges into the gas flow from the compressed gas supply conduit, whereby the constriction forms a nozzle in the dispensing tube. A spray device kit provides a medical spray device, a gas supply conduit, a pressure regulator, and a compressed gas container.

18 Claims, 3 Drawing Sheets

Figure 1:
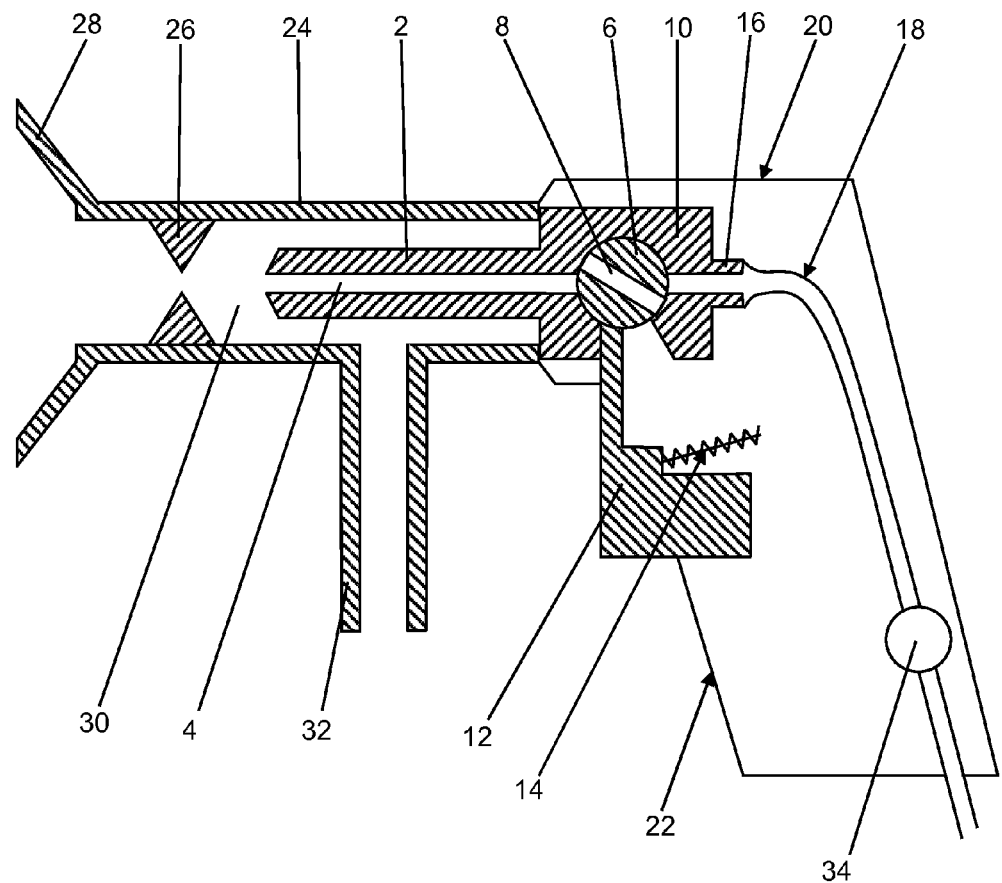

(51) Int. Cl.
*A61M 3/02* (2006.01)
*B05B 7/12* (2006.01)
*B05B 12/00* (2006.01)
*A61B 17/00* (2006.01)

(56) References Cited

U.S. PATENT DOCUMENTS

| | | | |
|---|---|---|---|
| 4,583,531 | A | 4/1986 | Mattchen |
| 5,306,237 | A | 4/1994 | Clement et al. |
| 5,520,667 | A * | 5/1996 | Roche ............... 604/290 |
| 5,542,918 | A | 8/1996 | Atkinson |
| 6,099,494 | A | 8/2000 | Henniges et al. |
| 6,595,968 | B1 | 7/2003 | Perrino |
| 6,635,035 | B1 | 10/2003 | Marasco et al. |
| 6,779,521 | B1 | 8/2004 | Schmehl et al. |
| 7,153,287 | B2 | 12/2006 | Henniges et al. |
| 2003/0036723 | A1 | 2/2003 | Henniges et al. |
| 2004/0122447 | A1 | 6/2004 | Harmon et al. |
| 2005/0177098 | A1 | 8/2005 | Lin et al. |
| 2011/0272437 | A1 | 11/2011 | Vogt et al. |
| 2013/0144211 | A1 * | 6/2013 | Vogt et al. ........ 604/131 |
| 2013/0180396 | A1 | 7/2013 | Vogt et al. |
| 2014/0364816 | A1 * | 12/2014 | Vogt ................ 604/290 |
| 2014/0364817 | A1 * | 12/2014 | Vogt ................ 604/290 |
| 2014/0364818 | A1 * | 12/2014 | Vogt ................ 604/290 |

FOREIGN PATENT DOCUMENTS

| | | |
|---|---|---|
| DE | 2451367 A1 | 5/1975 |
| DE | 2808499 A1 | 9/1978 |
| DE | 19536748 A1 | 5/1997 |
| DE | 19944208 C1 | 9/2001 |
| DE | 102009021421 A1 | 11/2010 |
| DE | 102010046057 B3 | 1/2012 |
| GB | 1493614 A | 11/1977 |
| JP | H4-56259 | 5/1992 |
| JP | 06 52839 H U | 7/1994 |
| JP | 2000 117211 A | 4/2000 |
| JP | 2011 235282 A | 11/2011 |
| WO | 98/13470 A1 | 4/1998 |

OTHER PUBLICATIONS

Breusch, et al., "Zementierte Hüftendoprothetik—Verminderung des Fettembolierisikos mittels gepulster Druckspülung," Orthopädie, 2000, vol. 29, pp. 578-586, Heidelberg, Germany, English-language Abstract on p. 579.

Breusch, et al., "Lavage Technique in Total Hip Arthroplasty, Jet Lavage Produces Better Cement Penetration Than Syringe-Lavage in the Proximal Femur," The Journal of Arthroplasty; 2000, pp. 921-927, vol. 15, No. 7; Churchill Livingstone; Heidelberg, Germany.

Christie, et al., "Medullary Lavage Reduces Embolic Phenomena and Cardiopulmonary Changes During Cemented Hemiarthroplasty," British Editorial Society of Bone and Joint Surgery; May 1995, vol. 77-B, No. 3, pp. 456-459, United Kingdom.

Byrick, et al., "High-volume, High-Pressure Pulsatile Lavage During Cemented Arthroplasty," The Journal of Bone and Joint Surgery, Incorporated; Oct. 1989, vol. 71-A, No. 9, pp. 1331-1336, Toronto, Ontario, Canada.

German Office Action for corresponding German Application No. 10 2012 013 464.9 dated Feb. 21, 2013.

English translation of the Notice of Reasons for Rejection issued in corresponding Japanese Application No. 2013-089715 dated May 20, 2014.

Patent Examination Report No. 1 issued in corresponding Australian Application No. 2013204645 on May 23, 2014.

Chinese Office Action for corresponding Chinese Application No. 201310164182.1 dated Sep. 21, 2015.

* cited by examiner

LAVAGE SYSTEM HAVING A NOZZLE

The invention relates to a medical spray device, in particular lavage system, comprising a compressed gas supply conduit for generating a gas flow, a liquid supply conduit for supplying a liquid, a dispensing tube having an open tube end for spraying fine droplets or a spray mist of a liquid-gas mixture, and an operable valve element that is arranged in the compressed gas supply conduit. The invention also relates to a spray device kit comprising a medical spray facility of this type.

Medical spray devices are used to generate a spray jet or spray cone made of a gas-liquid mixture for cleaning a wound, a cavity, an implant or a body part.

Lavage systems are used widely in surgery as medical spray devices to clean tissue areas. Specifically during the implantation of articular endoprostheses and during septic revisions, lavage systems have essential significance (R. M. Sherman et al.: "The role of lavage in preventing hemodynamic and blood-gas changes during cemented arthroplasty" J. Bone Joint. Surg. 1983; 65-A: 500-506; S. J. Breusch et al.: Zementierte Hüftendoprothetik: Verminderung des Fettembolierisikos in der zementierten Hüftendoprothetik mittels gepul-ster Druckspülung, Orthopädie 2000; 29: 578-586; S. J. Breusch et al.: Lavage technique in THA: Jet-lavage Produces Better Cement Penetration Than Syringe-Lavage in the Proximal Femur; J. Arthroplasty. 200; 15(7): pages 921-927; R. J. Byrick et al.: High-volume, high pressure pulsatile lavage during cemented arthroplasty; J. Bone Joint Surg. 1989; 81-A: pages 1331-1336; and J. Christie et al.: Medullary lavage reduces embolic phenomena and cardiopulmonary changes during cemented hemiarthroplasty, J. Bone Joint Surg. 1995; 77-B: pages 456-459). Tissue areas are cleaned during lavage by means of spray puffs of suitable rinsing liquids, such as isotonic saline solutions. Up to several thousand spray puffs per minute are common in this context.

Pulsed lavage systems have been known for a long time. Unexamined patent specifications U.S. Pat. No. 4,583,531 A, U.S. Pat. No. 4,278,078 A, and U.S. Pat. No. 5,542,918 A shall be cited in this context for exemplary purposes. Lavage systems that are currently being marketed are driven through electrical motors (for example, InterPulse® Jet lavage made by Stryker GmbH & Co. KG) or compressed air (for example, PALAVAGE® made by Heraeus Medical GmbH).

US 2003 036 723 A1 discloses a lavage system having a pump that is driven by means of an electrical motor via a gear. Said pump generates the jet of liquid. The energy for the motor is supplied through an electrical cable.

DE 10 2009 021 421 A1 proposes a jet lavage having a lifting magnet driving the membrane pump.

Compressed air-driven systems usually utilise a compressed air motor as their drive. In most systems, this concerns a vane-type compressed air motor. The compressed air motor generates a rotary motion which is then converted into an oscillating linear motion. The oscillating linear motion is utilised to convey momentum to small volumes of a rinsing medium. It is common in this context to arrange at least one membrane between the drive and the inlet of rinsing liquid in order to be able to transmit the pulses to the rinsing liquid. This generates spray puffs. At high pulse rates of 2,000 to 3,000 pulses per minute, volumes in the range of several hundred milliliters of rinsing liquid are sprayed. This means that the compressed air motor needs to be manufactured at high precision in order to tolerate such high rotation rates. Moreover, sufficiently stable storage must be available. For these reasons, the compressed air motor is the most expensive component of common compressed air-driven lavage systems. Therefore, the compressed air motor is generally arranged in a handle made of metal or other durable materials such that this component can be used multiply after appropriate reprocessing and sterilisation.

Battery-operated lavage systems have also proven useful. However, a large battery block, which only has a limited charge capacity due to its nature, always needs to be taken along. Compressed air-driven lavage systems are advantageous by comparison in that compressed air is available in unlimited quantities in many operating theatres and thus allow rinsing liquid to be sprayed for any desired time without the energy supply being limited. However, one problem is that a compressed air hose invariably needs to connect the lavage system to the stationary compressed air conduit.

Sterile water and aqueous solutions that can just as well contain pharmaceutically active substances can be used as liquid for lavage systems. The rinsing water containing the residues can be aspirated by the lavage system through a second channel.

A generic lavage system, in which a linearly oscillating pestle is driven through a compressed gas motor which can be supplied with compressed gas through an operable valve is known from DE 10 2010 046 057 B3. The pestle periodically hits onto a membrane of the lavage system and thus forms a membrane pump in periodical operation for generating a pulsating jet of liquid.

The complex structure of said lavage system is disadvantageous. Due to the hygienic requirements, at least parts of the lavage system need to be sterilisable or the lavage system needs to be a disposable product that is as inexpensive as possible.

It is the object of the present invention to overcome these and other disadvantages that have not been specified above. In particular, a less expensive system is to be provided that is easy to insert and can be designed to be resource-saving.

The invention is also based on the object to develop a simple medical spray device that consists of a minimal number of parts and is driven through compressed gas. The driving device should largely consist of inexpensive materials that can be fabricated through simple procedures. This should enable provision of a medical spray device for single use at low manufacturing and assembly costs. Expensive, rotating or moving parts requiring precise, stable support like in a bearing should be minimised.

Said objects are met by a medical spray device, in particular a lavage system, comprising a compressed gas supply conduit for guiding a gas flow, a liquid supply conduit for supplying a liquid, a dispensing tube having an open tube end for spraying fine droplets or a spray mist of a liquid-gas mixture, and an operable valve element that is arranged in the compressed gas supply conduit, whereby a constriction of the cross-sectional area is provided in the dispensing tube and a merging site is arranged in the region of the constriction through which the liquid merges into the gas flow from the compressed gas supply conduit, whereby the constriction forms a nozzle in the dispensing tube.

The constriction of the cross-sectional area reduces the internal cross-section of the outflow tube in this context. Accordingly, the cross-section of the conduit formed by the outflow tube is reduced.

In this context, the invention can provide an aspiration facility connected to an aspiration conduit to be situated in the region of the open tube end of the dispensing tube, whereby the aspiration facility preferably comprises an aspiration tube into which the aspiration conduit merges, and whereby the aspiration tube particularly preferably surrounds the dispensing tube.

The aspiration facility can be used to aspirate residues that become detached by the spray.

Moreover, the invention can provide a funnel to be arranged at the extreme tube end, in particular at the dispensing tube or at the aspiration facility, which funnel is suitable for limiting and/or aligning the spray cone produced.

If the spray device also has an aspiration facility, the aspiration effect is also being directed by the funnel.

According to a particularly preferred embodiment of the invention, the valve element is a rotary valve, in particular a rotationally symmetrical rotary valve, preferably a conical or cylindrical rotary valve, having a passage, whereby the rotary valve is supported like in a bearing, such that it can be rotated, in a recess in an outflow body that defines a part of the compressed gas supply conduit, whereby the rotary valve preferably can be operated through a trigger, whereby it is particularly preferable for the rotary valve and the trigger to be provided as a same part.

Rotary valves of said design can be manufactured inexpensively and can be inserted easily into corresponding recesses of the spray devices. As a matter of principle, other valve elements that can be controlled, for example, by electrical means are conceivable just as well. However, said valve elements are more resource-consuming to manufacture and are thus more expensive. Moreover, a voltage source may need to be provided, if applicable.

Therefore, it is particularly preferred to have a rotary valve as valve element. In the simplest case, rotary valves consist of just a cylinder or cone that contains at least one patent bore hole, whereby the cylinder or cone is arranged in a simple cylinder-shaped or cone-shaped valve seat. Accordingly, rotary valves can be manufactured inexpensively and relatively simply through injection moulding of plastic materials.

Another refinement of a spray device according to the invention can provide the valve element to be maintained in the closed state by means of a spring element, whereby the spring element preferably is attached on one side on the trigger.

Said design would be easier to operate than if the valve element had to be closed through an active action.

Particularly preferably, the invention can provide the spray device to consist essentially of plastic material, preferably of thermoplastic material, particularly preferably of thermoplastic material suited for gamma-sterilisation, whereby in particular the dispensing tube, valve element, compressed gas supply conduit, funnel, aspiration tube, outflow body and/or the constriction consist of plastic material.

Plastic materials are inexpensive in manufacturing. The use of thermoplastic materials allows the spray device to be manufactured inexpensively in large numbers through injection moulding. This allows the spray device to be manufactured cheaply enough for use as a disposable article. Plastic materials suitable for gamma sterilisation are particularly well-suited for medical applications in order to meet the strict clinical requirements for medical products in the field of surgery.

According to a variant of the invention that is particularly inexpensive in design, the compressed gas supply conduit is provided, at least over regions thereof, as outflow tube that is surrounded, at least over regions thereof, in particular fully, by the dispensing tube, whereby the compressed gas supply conduit preferably merges into the dispensing tube through a supply nozzle.

A refinement of the invention can provide the merging site to be arranged upstream of the nozzle with respect to the direction of flow.

In this context, the invention can provide, in particular, the constriction to be implemented through a circular ring having a triangular cross-sectional area, whereby one of the corners of the triangular cross-sectional area is oriented towards the middle of the ring.

Alternatively, the invention can provide the merging site to be situated in the constriction, whereby the nozzle preferably is a Venturi nozzle.

This allows a particularly well-directed jet and/or cone to be generated.

The invention can just as well provide the spray device to comprise a compressed gas container that is preferably filled with liquid carbon dioxide, whereby the compressed gas container is preferably arranged in a handle part.

Said embodiment is independent of whether or not a compressed gas supply conduit or compressor is present in the place where it is used. Said spray devices are particularly well-suited for mobile use.

A particularly preferred refinement of the invention provides the spray device to comprise a settable pressure reducer that can be used to set the gas pressure in the compressed gas supply conduit.

The pressure of the jet and/or spray cone can be matched to suit the tissue or material to be treated. For this reason, a spray device of this type has a broader range of applications.

The invention can particularly preferably provide a second nozzle to be arranged, preferably to be formed through the outflow tube, at the end of the compressed gas supply conduit through which the flowing gas exits from the compressed gas supply conduit in the direction of the constriction.

Said second nozzle generates a gas flow that is particularly well-suited for generating the gas-liquid spray mist and promotes a chaotic, pulse-like ejection of puffs of liquid.

The objects of the invention are also met through a spray device kit comprising a medical spray device of this type, a gas supply conduit, in particular flexible gas supply conduit, a pressure regulator, and a compressed gas container.

The invention is based on the surprising finding that the constriction in the dispensing tube in combination with the attendant forces upon a flow through said constriction allows a gas-liquid spray jet and/or a gas-liquid spray cone to be generated, in which the liquid droplets are entrained through the gas flow. The spray jet thus generated is suitable for medical treatment. The stochastic and chaotic entrainment of liquid droplets causes non-periodical pulses to be generated that surprisingly lead to a good cleaning effect as tests of the inventors have shown. Simultaneously, the spray jet is steadier though and a comparable cleaning effect can be attained in less time as compared to known lavage systems and/or medical spray devices.

The medical spray device is based on compressed gas firstly being guided through the compressed gas supply conduit to the valve element. Opening the valve element allows the compressed gas to flow into the outflow tube and then through an open end of the outflow tube, which is provided as a second nozzle, into the dispensing tube where it passes by the constriction. The constriction increases the flow velocity of the gas and/or gas-liquid mixture and a negative pressure is generated perpendicular to the direction of flow. Said negative pressure aspirates liquid out of the liquid intake. The aspirated liquid moves towards the nozzle formed by the constriction and mixes with the flowing gas flow. This produces a liquid-gas spray jet. Said spray jet contains finely distributed liquid droplets and exits from the dispensing tube at its open tube end.

Accordingly, a medical spray device according to the invention can be made up as follows from:

a) a compressed gas supply conduit;
b) a valve element that is connected to the compressed gas supply conduit;
c) a hollow outflow tube that is connected to the valve element and is provided as a nozzle at its end facing away from the valve element;
d) a dispensing tube having an open tube end and a closed tube end that surrounds the outflow tube;
e) at least one constriction in the dispensing tube, whereby the constriction is arranged in the direction of the open tube end with respect to the nozzle of the outflow tube; and
f) a liquid intake that is connected to the dispensing tube in liquid-permeating manner, whereby the liquid intake is arranged downstream of the nozzle of the outflow tube with respect to the open end of the tube.

Due to its simplicity, the driving device according to the invention can be manufactured advantageously as a single-use article.

A third nozzle can be attached to the open end of the dispensing tube to control the geometry of the spray jet, if applicable. Said third nozzle can contain one or more openings that are arranged according to the desired geometry of the spray jet.

The invention can just as well provide the spray device to be arranged in a housing, whereby at least regions of the housing are provided as a handle, particularly preferably are provided as a pistol-like handle.

Advantageously, the valve element is connected to a trigger that is pressed into the closed state by means of a spring. In this context, the spring and parts of the trigger are supported like in a bearing inside the housing.

Moreover, a spray device kit according to the invention having a spray device according to the invention can comprise a flexible gas supply conduit, a pressure regulator, and a compressed gas container.

Conceivable compressed gas containers and/or compressed gas cartridges are all cartridges filled with non-toxic gases, in particular metal cartridges. Liquid carbon dioxide-filled cartridges are particularly preferred, though. Carbon dioxide is non-toxic, non-combustible, non-explosive, and inexpensive. A large gas volume can be stored in small cartridges in the form of liquid carbon dioxide.

The particular advantage of the spray device kit is that no stationary compressed air supply conduits are required, while a forceful spray jet can still be generated. The use of compressed gas is not associated with a fire or explosion hazard such as may be the case with electrical drive devices. There is also no need to have battery blocks or rechargeable battery blocks present.

The various embodiments of the invention are simple implementation variants reflecting the scope of the invention. The design of the spray device remains quite simple in all cases.

Figure 2:
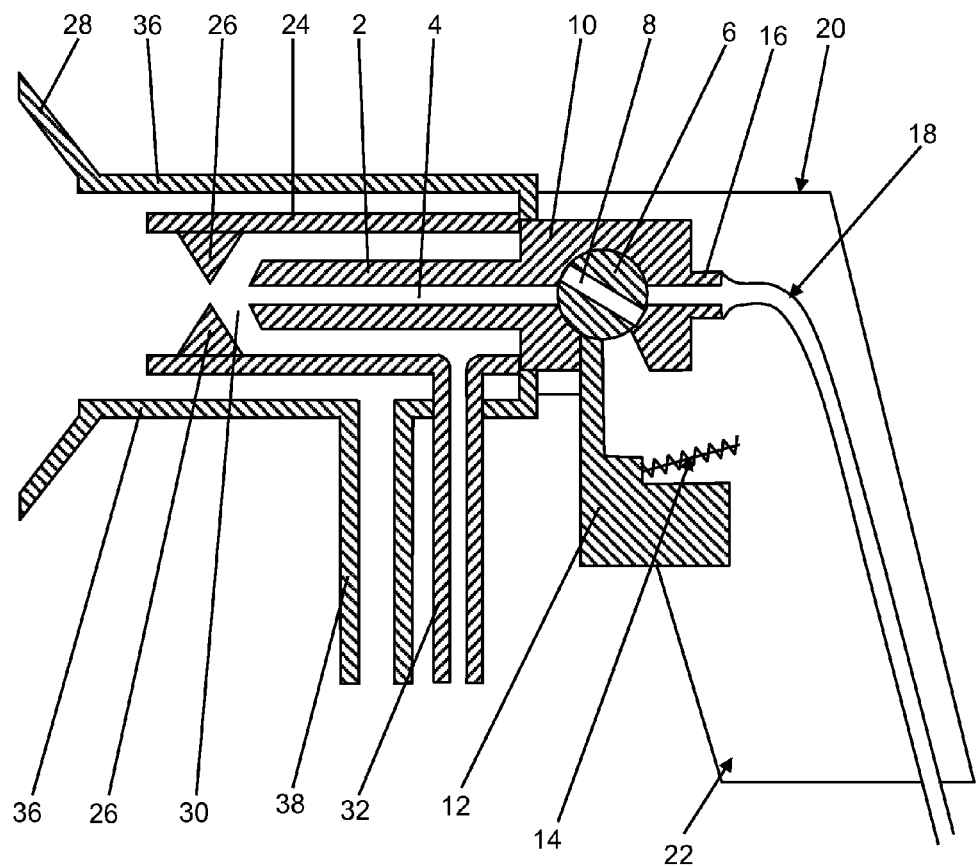
Figure 3:
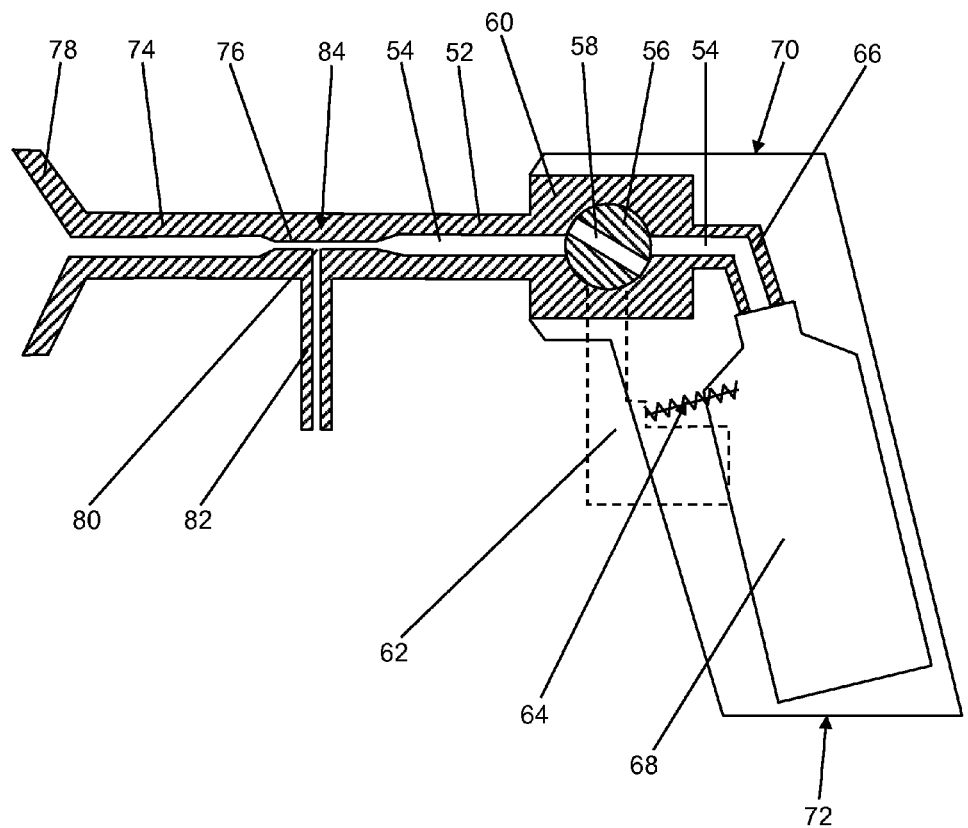

Exemplary embodiments of the invention shall be illustrated in the following on the basis of three schematic figures, though without limiting the scope of the invention. In the figures:

FIG. 1: shows a schematic cross-sectional view of a spray device according to the invention;

FIG. 2: shows a schematic cross-sectional view of an alternative spray device according to the invention having an aspiration facility; and FIG. 3: shows a schematic cross-sectional view of a third spray device according to the invention having a Venturi nozzle.

FIG. 1 shows a schematic cross-sectional view of a spray device according to the invention. The core of the spray device is made up by an outflow tube 2 having a compressed gas supply conduit 4. A rotary valve 6 having a feed-through 8 is arranged in the compressed gas supply conduit 4. The feed-through 8 has the same cross-section as the compressed gas supply conduit 4 and connects the compressed gas supply conduit 4 in the open position of the rotary valve 6 and forms an extension of the compressed gas supply conduit 4. The rotary valve 6 can be inserted or pressed-in as a conical component into an outflow body 10 of the outflow tube 2. The rotary valve 6 can be operated by means of a trigger 12.

A restoring element 14 in the form of an elastic steel spring 14 is provided at the trigger 12. A spring guide rod is situated inside the spring 14. A hose 18 that is or can be connected to a compressed gas source is secured to a socket 16 that forms an extension of the outflow tube 2 and/or of the compressed gas supply conduit 4. The outflow body 10 and the remaining rear part of the spray device are accommodated in a housing 20 that forms a handle 22 in the back that is similar to a pistol handle. The spring 14 is connected to the trigger 12 and the housing 20 and ensures that the trigger 12 remains in the position shown and that the rotary valve 6 therefore stays closed. Taking the lavage system with one hand, the trigger 12 can be operated like in a pistol using the fingers of the same hand against the spring force of the spring 14 and the rotary valve 6 can thus be opened. As soon as the trigger 12 is released, the valve element 6 also closes again.

The outflow tube 2 merges via a valve (not shown) in a dispensing tube 24 that surrounds the outflow tube 2 at a distance therefrom. When a compressed gas flows through the compressed gas supply conduit 4 into the dispensing tube 24 with the rotary valve 6 being open, it encounters at this site just downstream of the end of the outflow tube 2 a constriction 26 that accelerates the gas in the manner of a nozzle. A funnel 28 is arranged at the end of the dispensing tube 24.

The acceleration of the gas in the region of the constriction 26 generates a negative pressure in the region of the merging site 30. Said negative pressure aspirates a liquid through a liquid supply conduit 32 which is then entrained in the region of the inlet by the gas flow from the outflow tube 2. In the process, droplets of liquid are generated and mix with the gas flow. Lastly, the gas flow mixed with the liquid droplets is ejected through the funnel 28.

A rotary switch (not shown) is provided at the handle 22 and can be used to set a pressure reducer 34 that is arranged in the gas supply conduit 18 and/or the hose 18, as the case may be. The pressure reducer 34 can be used to set the gas pressure that arrives at the socket 16 and exerts its effect through the compressed gas supply conduit 4 also in the region, in which the gas flow is being mixed with the liquid. The gas pressure is also crucial for the strength and/or volume flow of the spray cone that exits from the funnel 28 and/or is generated by the spray device. This allows the strength of the spray cone to be set. If the spray cone is desired to have just a single strength and/or if a particularly inexpensive variant of the spray device is desired, it is feasible to forego the pressure reducer 34.

The medical spray device can be used as a variable lavage system, in which the strength and thus the effect of the spray cone can be set. The source of compressed gas can be a central compressed gas facility or the hose 18 can just as well be connected to a $CO_2$ cartridge or to a compressor for generating the requisite gas pressure.

The entire spray device except for the spring 14 and the pressure reducer 34 can be manufactured inexpensively from plastic materials.

FIG. 2 shows a schematic cross-sectional view of an alternative embodiment of a spray device according to the invention. The spray device is basically designed like the one according to FIG. 1, except that the pressure reducer 34 was left out and an aspiration facility was provided in addition. For this purpose, an aspiration tube 36 is arranged about the dispensing tube 24 and comprises an aspiration conduit 38 and a feed-through for the liquid supply conduit 32. The funnel 28 is arranged at the outermost tube 36, i.e. at the aspiration tube 36 in the present case.

A negative pressure is being applied to the aspiration conduit 38, or a pump is being connected that generates a minor negative pressure that is sufficient to aspirate liquid residues dripping off the front edge of the dispensing tube 24 and the spent liquid. The aspiration facility is preferably used to aspirate the liquid contaminated by tissue. A negative pressure in the range of 50 mbar to 400 mbar is sufficient for this purpose. The fast gas-liquid jet and/or cone is not aspirated in the process, since the momentum of the jet and/or cone is too high for this to occur.

The embodiment of the spray devices according to FIGS. 1 and 2 by means of tubes 2, 24, 36 that are arranged one inside the other and at a distance from each other is meant to render the manufacturing of the spray devices particularly easy and inexpensive. The tubes 2, 24, 36 having the supply and discharge conduits 32, 38, rotary valve 6, trigger 22, housing 20, outflow body 10, socket 16, and funnel 28 can be manufactured as plastic parts by means of an injection moulding method and are easy to assemble.

FIG. 3 shows a schematic cross-sectional view of another embodiment of the invention. The medical spray device shown comprises an outflow tube 52 that limits a front region of a compressed gas supply conduit 54. A rotary valve 56 is arranged in the compressed gas supply conduit 54 and comprises a feed-through 58 that has the same cross-section as the compressed gas supply conduit 54 and extends and connects the compressed gas supply conduit 54 when the rotary valve 56 is in its open position. The rotary valve 56 is inserted into an outflow body 60 in the same manner as the rotary valve 6 according to FIGS. 1 and 2 and can be operated in the same manner by means of a trigger 62 having a restoring spring 64.

The trigger 62 is indicated through dashed lines in FIG. 3 since it is not situated in the image plane. It is preferable for the trigger 62 not to be situated in the same plane as the feed-through 58 through the rotary valve 56 in order to ensure the design freedom for structuring the trigger 62 and outflow body 60. The outflow body 60 then does not need to have a recess at the site at which this would otherwise be required by the mobility of the trigger 62. A recess of this type, such as shown in FIGS. 1 and 2, might be in the way of the compressed gas supply conduits 4, 54. Moreover, there is a risk that the feed-through 8, 58 might inadvertently be connected to the surroundings by means of said recess. Accordingly, the embodiments according to FIGS. 1 and 2, just like the preferred embodiment according to FIG. 3, preferably provide the trigger 12, 62 to be offset with respect to the plane of the feed-through 8, 58.

A connector 66 forming an extension of the compressed gas supply conduit 54 connects a compressed gas cartridge 68 that supplies a gas pressure to the spray device. The connector 66 has a pressure reducer (not shown) provided inside it that can be operated from outside and is used to set the gas pressure supplied from the compressed gas cartridge 68 into the compressed gas supply conduit 54. The compressed gas cartridge 68 is arranged in the handle part 72 of a housing 70.

The outflow tube 52 merges through a constriction 76 into a dispensing tube 74. The dispensing tube 74 is open to the outside to the surroundings via a funnel 78 for aligning and limiting a spray cone that is to be generated using the spray device. A merging site 80 is provided in the region of the constriction 76 and connects a liquid supply conduit 82 to the feed-through in the constriction 76, whereby the feed-through is interpreted to be a part of the dispensing tube 74 such that the constriction 76 is considered to be a part of the dispensing tube 74 in the present case. The liquid supply conduit 82 hits perpendicularly on the feed-through in the constriction 76 and forms a Venturi nozzle 84 therein.

The cross-section inside the constriction 76 is reduced as compared to the cross-sections of the compressed gas supply conduit 54 and dispensing tube 74. The gas flowing from the compressed gas cartridge 68 through the conduits is accelerated in the region of the constriction 76. According to Bernoulli and Venturi, this generates a negative pressure in the liquid supply conduit 82 by means of which liquid in the region of the merging site 80 is entrained by the gas flow through the Venturi nozzle 84. This generates a gas-liquid mixture that is sprayed out through the funnel 78 and/or the opening of the dispensing tube 74, as the case may be.

The outflow tube 52, dispensing tube 74, outflow body 60, funnel 78, and connector 66 can be manufactured as the same part made of plastic material. Likewise, the valve element 56 and the trigger 62 can be manufactured as the same part made of plastic material.

Preferably, a thermoplastic material can be used for all plastic parts of all embodiments according to FIGS. 1, 2, and 3.

The features of the invention disclosed in the preceding description and in the claims, figures, and exemplary embodiments, can be essential for the implementation of the various embodiments of the invention both alone and in any combination.

LIST OF REFERENCE NUMBERS 2, 52 Outflow tube
4, 54 Compressed gas supply conduit
6, 56 Rotary valve/valve element
8, 58 Feed-through
10, 60 Outflow body
12, 62 Trigger
14, 64 Spring
16 Connector
18 Hose
20, 70 Housing
22, 72 Handle/handle part
24, 74 Dispensing tube
26, 76 Constriction/first nozzle
28, 78 Funnel
30, 80 Merging site
32, 82 Liquid supply conduit
34 Pressure reducer
36 Aspiration tube
38 Aspiration conduit
66 Connector/connecting tube
68 Compressed gas cartridge
84 Venturi nozzle

The invention claimed is:

1. A medical spray device comprising
an outflow tube having a compressed gas supply conduit for generating a gas flow,
a dispensing tube connected to a liquid supply conduit for supplying a liquid, wherein the dispensing tube has a total length defined between a first end and a second end located opposite with respect to the first end of the dispensing tube, wherein the first end of the dispensing tube is an open end for spraying fine droplets or a spray mist of a liquid-gas mixture, and an outflow body having an operable valve element arranged in the compressed gas supply conduit, wherein a constriction of a cross-sectional area is provided in the dispensing tube and a merging site is arranged in the region of the constriction through which the liquid merges into the gas flow from the compressed gas supply conduit, wherein the constriction forms a nozzle in the dispensing tube, and further wherein a portion of the dispensing tube surrounds the outflow tube, the outflow tube is connected and adjacent to the outflow body, and the second end of the dispensing tube contacts a portion of the outflow body.

2. The medical spray device according to claim 1, wherein the valve element is a rotationally symmetrical rotary valve.

3. The medical spray device according to claim 1, wherein the valve element is a conical or cylindrical rotary valve.

4. The medical spray device according to claim 1, wherein the constriction is implemented through a circular ring having a triangular cross-sectional area, whereby one corner of the triangular cross-sectional area is oriented towards a middle of the circular ring.

5. The medical spray device according to claim 1, further comprising a compressed gas container fillable with liquid carbon dioxide, wherein the compressed gas container is arranged in a handle part.

6. The medical spray device according to claim 1, further comprising a settable pressure reducer configured to set a gas pressure in the compressed gas supply conduit.

7. The medical spray device according to claim 1, further comprising a second nozzle arranged at an end of the compressed gas supply conduit through which the flowing gas exits from the compressed gas supply conduit in a direction of the constriction.

8. The medical spray device according to claim 1, wherein the spray device consists essentially of thermoplastic material configured for gamma-sterilisation.

9. The medical spray device according to claim 1, further comprising an aspiration facility, connected to an aspiration conduit, in the region of the open end of the dispensing tube, whereby the aspiration facility comprises an aspiration tube into which the aspiration conduit merges, and whereby the aspiration tube surrounds the dispensing tube.

10. The medical spray device according to claim 9, further comprises a funnel arranged at the dispensing tube or at the aspiration facility, wherein the funnel is configured to limit or align a spray cone produced by the device.

11. The medical spray device according to claim 1, wherein the valve element is a rotary valve having a passage, whereby the rotary valve is supported such that the rotary valve is rotatable in a recess in an outflow body that defines a part of the compressed gas supply conduit, whereby the rotary valve is operable through a trigger, whereby the rotary valve and the trigger are a same part.

12. The medical spray device according to claim 11, wherein the valve element is maintained in the closed state by means of a spring element, whereby the spring element is attached on one side on the trigger.

13. The medical spray device according to claim 1, wherein the compressed gas supply conduit merges into the dispensing tube at the merging site through a supply nozzle.

14. The medical spray device according to claim 13, wherein the merging site is arranged upstream of the supple nozzle with respect to a direction of flow.

15. The medical spray device according to claim 13, wherein the merging site is situated in the constriction, wherein the supply nozzle is a Venturi nozzle.

16. A spray device kit comprising
the medical spray device according to claim 1,
a gas supply conduit,
a pressure regulator, and
a compressed gas container.

17. The spray device kit according to claim 16, wherein the gas supply conduit is a flexible gas supply conduit.

18. A medical spray device comprising:
an outflow tube having a compressed gas supply conduit for generating a gas flow, a dispensing tube connected to a liquid supply conduit for supplying a liquid, wherein the dispensing tube has a length defined between a first end and a second end located opposite with respect to the first end of the dispensing tube, wherein the first end of the dispensing tube is an open end for spraying fine droplets or a spray mist of a liquid-gas mixture, and an outflow body having an operable valve element arranged in the compressed gas supply conduit, wherein the outflow tube and the outflow body are integrally formed together, wherein a constriction of a cross-sectional area is provided in the dispensing tube and a merging site is arranged in the region of the constriction through which the liquid merges into the gas flow from the compressed gas supply conduit, wherein the constriction forms a nozzle in the dispensing tube, and further wherein a portion of the dispensing tube surrounds the outflow tube.

* * * * *